United States Patent [19]
Yamamoto

[11] Patent Number: 5,841,884
[45] Date of Patent: Nov. 24, 1998

[54] WATER QUALITY MONITORING APPARATUS

[75] Inventor: Takahiro Yamamoto, Fukuoka, Japan

[73] Assignee: Anima Electronics Co., Ltd., Fukuoka, Japan

[21] Appl. No.: 744,823

[22] Filed: Nov. 6, 1996

[30] Foreign Application Priority Data

Nov. 6, 1995 [JP] Japan ................................. 7-287576

[51] Int. Cl.$^6$ ............................. G06K 9/00; H04M 7/18
[52] U.S. Cl. ............................................ 382/110; 348/81
[58] Field of Search .................................... 382/100, 110; 348/81, 135; 119/215

[56] References Cited

U.S. PATENT DOCUMENTS 4,963,035 10/1990 McCarthy et al. ...................... 382/110

*Primary Examiner*—David K. Moore
*Assistant Examiner*—Hieu C. Le

*Attorney, Agent, or Firm*—Wenderoth, Lind & Ponack, L.L.P.

[57] ABSTRACT

A water quality monitoring apparatus including a raw water supply and discharge unit 7 equipped with a monitoring water tank 5 for breeding fish under observation. The raw water supply and discharge unit 7 is detachably placed in a lower section of a rack 1, and a video camera 8 is provided in opposed relation to the monitoring water tank 5. Also included are a fish detecting sensor 10 for detecting an actional pattern or the like of the fish under observation on the basis of a picture from the video camera 8 and a computer 11 for detecting the abnormality of the water quality on the basis of the detection result of the fish actional pattern or the like. The raw water supply and discharge unit 7 is made to be drawn from the rack 1 lower section, for example, at the time of cleaning its tanks. Thus, the maintenance thereof becomes easily possible, besides the entire apparatus becomes reducible in dimension to make the space necessary for the installation smaller.

13 Claims, 12 Drawing Sheets

WATER QUALITY MONITORING APPARATUS

BACKGROUND OF THE INVENTION

1. Field of the Invention

The present invention relates to a water quality monitoring apparatus which introduces raw water into a breeding water tank to photograph or image-capture fish swimming in the water tank through a video camera or the like to monitor the quality of the raw water on the basis of the action or the like of the fish under observation by means of the image analysis.

2. Description of the Related Art

So far, as exemplified by Japanese Patent Publication Nos. 6-16034 and 6-68489 there has been known an apparatus which photographs fish being under observation and swimming in a raw water supplied water tank to monitor the quality of the raw water through the image analysis of, for example, the actional patterns of the fish taken for when poison or the like is mixed into the raw water. In such a prior apparatus, a filtering tank for filtering raw water, a breeding water tank and others are individually provided and coupled through water supply pipes to each other and the raw water is fed from the upper side of the breeding water tank, and a video camera is placed to be in opposed relation to the front of breeding water tank, moreover an image processing unit and a computer are separately and appropriately arranged in relation to the camera and electrically connected to each other, so that these equipment compose one water quality monitoring apparatus as a whole.

There is a problem which arises with such a prior apparatus, however, in that, because of easy growth of aquatic plant such as duckweed in the water tank, the growing duckweed can adhere onto a wall surface of the water tank which is within the photographing area of the camera to lead to failures in fish-position detecting operation depending upon the image taken by the camera, besides dust and the like attached thereto and accumulated thereon within the photographing area can also causes such failures. For these reasons, it is strongly desired to realize a breeding water tank free from the attachment of the duckweed and dust thereto.

In addition, although the decision on the abnormality of the water quality based on the actional analysis of fish relies upon the condition that the fish is in good health, since the prior water tank is not designed to create a water stream close to that of the natural rivers or the like, the fish may be subjected to stress to take an abnormal action or to lose his life, with the result that an erroneous decision on the water quality can take place.

Furthermore, because of the separate disposition of a plurality of tanks and a plurality of electronic equipment, the above-mentioned prior apparatus needs a large space for the disposition. In addition, difficulty is experienced to change its location after the installation, and even the tanks thereof require periodic cleaning.

SUMMARY OF THE INVENTION

The present invention has been developed with a view to eliminating these disadvantages, and it is therefore an object of the present invention to provide a water quality monitoring apparatus which is capable of breeding or feeding fish in an almost natural situation and of producing a monitoring tank where the duckweed growth and the dust attachment are suppressible, with the monitoring apparatus being wholly accommodated within one housing and a raw water supply and discharge unit requiring cleaning or the like being constructed as one unit and housed in the same housing to be detachable or removable to extremely facilitate maintenance.

In accordance with a first aspect of the preset invention, a water quality monitoring apparatus comprises a monitoring water tank for accommodating raw water to breed fish under observation in the raw water and a video camera for photographing the fish under observation from a front side of the monitoring water tank, image analysis means for analyzing an image taken through the video camera to monitor the quality of the raw water within the monitoring water tank, the monitoring water tank being composed of an inflow opening (inlet) made in one side surface thereof to define a first water flowing path extending from the one side surface to the other side surface thereof, a plurality of straightening plates, each having a plurality of water communicating holes, disposed perpendicularly in the first water flowing path to be separated from each other to define monitoring sections therebetween which breed the fish under observation therein, a perforated plate having a plurality of water-communicating holes and disposed below the first water flowing path and in parallel thereto to establish a second water flowing path coupled to the first water flowing path under the plurality of straightening plates, and an outflow opening (outlet) made in the second water flowing path.

The raw water introduced through the inflow opening in the side surface into the monitoring water tank passes through the straightening plates and flows toward the other side surface thereof to produce a straightened water stream along the first water flowing path in the monitoring sections. Accordingly, a situation close to the water stream in the natural rivers is attainable in the monitoring sections to release the fish from the stress concurrently with breeding the fish under observation in good condition. In addition, the perforated plate having a plurality of water communicating holes is located in parallel to the aforesaid water stream so that the monitoring sections are situated above the perforated plate, the water stream in the monitoring sections passes from the vicinity of the downstream side surface of the monitoring water tank through the perforated plate lower surface to the outflow opening, which establishes the second water flowing path. The duckweed and dust in the monitoring sections drop to reach the upper surface of the perforated plate and further fall through the plurality of water communicating holes toward below the perforated plate. At this time, since the second water flowing path is defined below the perforated plate, the dust and others fallen toward below the perforated plate do not flow in the opposite direction. Thus, because of the water steam at the front surface sides of the monitoring sections, the monitoring sections can always be maintained in a cleaned condition so that the growth of the duckweed is suppressible.

Furthermore, in accordance with a second aspect of this invention, a water quality monitoring apparatus comprises a filtering tank for filtering raw water, a monitoring water tank for accommodating the raw water filtered through the filtering tank and for breeding fish under observation in the raw water, a frame for supporting the filtering tank and the monitoring water tank, a plurality of wheels fitted on a lower portion of the frame, a raw water supply section for feeding the raw water into the filtering tank, a raw water introduction section for introducing the raw water filtered through the filtering tank into the monitoring water tank, a raw water discharge section for discharging the raw water from the monitoring water tank, a video camera for photographing the fish under observation within the monitoring water tank, and image analysis means for analyzing the image taken through the video camera to monitor the quality of the raw water within the monitoring water tank.

When the raw water is fed into the raw water supply section of the raw water supply and discharge means, the raw water is supplied from the raw water supply section into the filtering tank placed on the frame and, after filtered, introduced by the raw water introduction section into the monitoring water tank located on the frame and after passing through the monitoring water tank, further discharged from the raw water discharge section to the external, which establishes a series of water flowing paths from the introduction into the filtering tank to the discharge from the discharge section. Accordingly, the monitoring of the quality of the raw water is possible in such a manner that the fish under observation is bred within the monitoring water tank and photographed through the video camera or the like so that the image taken undergoes the image analysis. In addition, since the filtering tank and the monitoring water tank are together placed on the same frame, the whole structure of the apparatus is reducible in dimension, and since the frame is, at its lower portion, equipped with the wheels, the apparatus is freely movable together with the frame, which is extremely convenient in moving to a different place at cleaning of the tanks and in changing its installation location.

Still further, it is also possible that a water receiving tank is located on the aforesaid frame and is made to accept the raw water filtered through the filtering tank, and the raw water introduction section introduces the raw water within the water receiving tank into the monitoring water tank, with the water receiving tank and the filtering tank are constructed integrally with each other in a state that a partition plate is interposed therebetween. With this structure, the raw water filtered once comes into the water receiving tank and is subsequently introduced into the monitoring water tank by means of the raw water introduction section such as a pump. In this case, a water temperature gauge or the like can also be set within the water receiving tank to make the water temperature constant. Since this tank is provided integrally with the filtering tank in the frame with a partition being interposed therebetween, both the tanks are reducible in dimension.

Moreover, further included are a housing divided into upper and lower sections and a monitor television for displaying the image taken through the video camera. In the lower section of the housing there are detachably housed the frame together with the filtering tank and the monitoring water tank. In addition, in the lower section thereof there is accommodated the video camera which is located to be in opposed relation to the monitoring water tank. Moreover, in a side surface of the lower section of the housing there are made a water supply opening and a water discharge opening respectively coupled to the raw water supplying section and the raw water discharge section. On the other hand, the upper section of the housing is designed to accommodate the image analysis means. With this structure, the raw water flows from the water supply opening in the side surface of the housing and passes through the raw water supply section into the filtering tank and subsequently goes through the raw water introduction section into the monitoring water tank and thereafter exits from the discharge opening to the external by the aid of the raw water discharge section. The video camera in the housing photographs the monitoring water tank so that the image taken is displayed on the monitor television placed in the upper section of the housing and, at the same time, input to the image analysis means. This image analysis means analyzes the actional pattern of the fish under observation on the basis of the position of the fish or the like to decide, on the basis of the actional pattern, whether or not the quality of the raw water is in an abnormal condition. Since the raw water supply and discharge means, the monitor television and the image analysis means are situated within the single housing, the size reduction of the whole apparatus is possible and the location space is reducible. In addition, since the frame is detachably provided in an accommodating section of the lower section of the housing, for example at the cleaning of the water tanks the frame can readily be taken out from the lower section of the housing to be moved to a different place. Further, in the meantime, a frame with another raw water supply and discharge means can be housed and located within the lower section of the housing to continue the water quality monitoring operation.

Furthermore, an alarm means is set on the aforesaid housing to raise an alarm when the aforesaid image analysis means detects the abnormality of the water quality, and the screen of the monitor television is seen through a window made in a front surface of the upper section of the housing from the front side of the housing. With this structure, an image on the monitor television is checkable through the window made in the housing front surface to easily see the state of the monitoring water tank from the external. Further, in case that the abnormality of the water quality is found through the image analysis means, since the alarm means (for example, a warning buzzer or warning lamp) expresses warning, the operator or a managing person can know the abnormality of the water quality.

Still further, a ventilating opening is made in the housing and the monitoring apparatus is equipped with a ventilator coupled to the ventilating operation to ventilate the interior of the housing. Accordingly, the operation of this ventilator can ventilate the interior of the housing so that, for example, it is possible to prevent the breakdown of the image equipment and other devices coming from the corrosion caused by the generation of water vapor within the housing.

In addition, the monitoring water tank is composed of an inflow opening made in its own one side surface to produce a first water flowing path extending from the one side surface to the other side surface facing thereto and coupled to the aforesaid raw water introduction section, a plurality of straightening plates each having a plurality of water communicating holes and disposed in the first water flowing path to be perpendicular thereto and separated from each other to define monitoring sections for breeding fish under observation therebetween, a perforated plate having a plurality of water communicating holes and provided below and in parallel to the first water flowing path to form a second water flowing path coupled to the first water flowing path, and an outflow opening made on the second water flowing path and communicated with the raw water discharge section. Thus, the raw water introduced from the water supply opening in the housing side surface into the filtering tank in the lower section of the housing comes through the raw water introduction section into the monitoring water tank. Further, the raw water introduced through the inflow opening in the side surface into the monitoring water tank passes through the straightening plates to flow toward the other side surface thereof to be straightened in the monitoring sections to produce a water steam along the first water flowing path. Accordingly, it is possible to create an environment close to the natural rivers or the like within the monitoring sections to release the fish under observation from the stress so that the fish can be kept in a good condition. In addition, since the perforated plate having a plurality of water communicating holes is provided in parallel to the water stream and the monitoring sections are located above the perforated plate, the water stream within the monitoring sections goes from the vicinity of the downstream side surface of the monitoring water tank through the perforated plate to the outflow opening, which produces he second water flowing path. The dust, duckweed and the like sink within the monitoring sections to reach the upper surface of the perforated plate and then drop through the plurality of water communicating holes of the perforated plate. Since the second water flowing path is defined below the perforated plate, the dust and the like dropped to below the perforated plate do not head for the interiors of the monitoring sections. As a result, the water flows at the front surface sections of the monitoring sections so that the monitoring section can always be maintained in a cleaned condition to suppress the growth of the duckweed.

Moreover, in the apparatus according to the aforesaid first and second aspects, there are provided an overflow cylinder (or tube) placed outside the monitoring water tank and made such that its top portion is open, and a discharge tank located outside the overflow cylinder. The upper end portion of the overflow cylinder is slightly lower in position than the upper end portion of the monitoring water tank, and the interior of the overflow cylinder is communicated through the outflow opening with the monitoring water tank, so that the raw water overflown from the upper portion opening of the overflow cylinder is discharged through the discharge tank. With this structure, the raw water passing through the monitoring sections flows into the overflow cylinder and then overflows from the top surface thereof to enter the discharge tank. Since the upper end portion of the overflow cylinder is made to be lower in position than the top surface of the monitoring water tank, the water level within the monitor water tank can be kept to a level substantially equal to the position of the upper end portion of the overflow cylinder. In case that the inflow of the raw water from the inflow opening stops for some reason, the water level within the monitoring water tank falls. However, although the water level slightly lowers due to the counterflow at the inflow opening in the side surface thereof after it becomes lower than the upper end portion of the overflow cylinder, the water level does not become lower than the inflow opening. For this reason, the fish under observation does not die even if an unforeseen accident such as the fall of the water level occurs. Thus, it is possible to repair the breakdown portions afterwards and possible to quickly continue the monitoring operation after the water level is restored. In addition, since the dust or the like flowing out from the monitoring water tank through the outflow opening comes out through the overflow cylinder into the discharge tank, the dust, duckweed or the like onc flown out through the outflow opening does not return to the monitoring water tank, with the result that the interior of the monitoring water tank can always be maintained in a clean state.

In addition, the monitoring apparatus is equipped with detection means for detecting the filled condition and decreased condition of the raw water and alarm means for issuing an alarm on the basis of the detection of the filled condition and decreased condition of the raw water by the detection means. Since in the monitoring water tank there is provided the detection means for detecting the filled and decreased conditions of the raw water, in case that, for example, the raw water comes into the filled condition or an abnormally decreased condition due to the failure of the pump or the like, this situation is detectable to issue an alarm in accordance with its detection signal to inform the operator of this accident.

Furthermore, the image analysis means is provided with picture transmission means for transmitting a picture signal produced at the detection of the water quality abnormality to a communication line. With this provision of the picture transmission means, when the image analysis means detects the abnormality of the water quality, the picture transmission means sends the picture signal through the communication line (a public line or private line) to a monitoring center standing at a different place, so that the center can analyze the action of the fish under observation at the occurrence of the abnormality through a monitor television. Further, the monitoring center can give various kinds of instructions to the managing person or the like existing at the located place of the water quality monitoring apparatus on the basis of the analysis results.

BRIEF DESCRIPTION OF THE DRAWINGS

The object and features of the present invention will become more readily apparent from the following detailed description of the preferred embodiments taken in conjunction with the accompanying drawings in which.

DETAILED DESCRIPTION OF THE INVENTION

Figure 1:
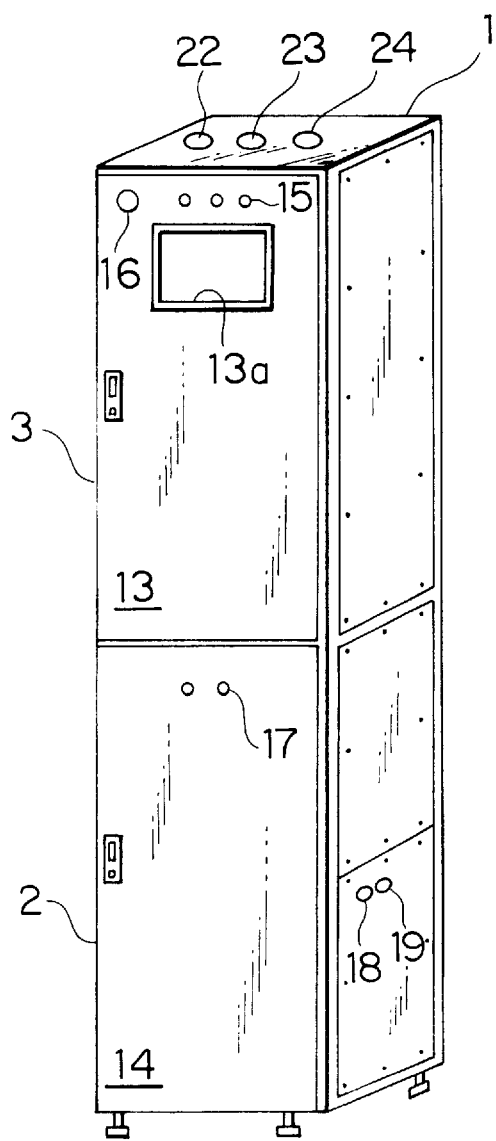
FIG. 1 is a perspective view showing a water quality monitoring apparatus according to an embodiment of the present invention.

A detailed description will be made hereinbelow of an embodiment of the present invention with reference to the accompanying drawings. First of all, the entire structure of a water quality monitoring apparatus according to this embodiment will be described with reference to FIGS. 1 to 3 which are perspective views and a rear elevational view showing the same apparatus. In the illustrations, numeral 1 represents a body rack (housing) constituting the external shape of this apparatus, which is divided into a lower section serving as a fish monitoring section 2 and an upper section acting as an image analysis section 3. In the fish monitoring section 2 being the lower section of the rack 1 there is removably accommodated a raw water supply and discharge unit 7 constructed by uniting a filtering water receiving tank 4, a monitoring water tank 5 for breeding fish, a water suction pump 36, and others. Further, on the top surface of the lower section of the rack 1 there is installed a video camera taking opposed relation to the monitoring water tank 5 of the supply and discharge unit 7. Still further, slope plates 6a, 6b are detachably or removably placed on the lower end portion of the fish monitoring section 2 of the rack 1, and casters 26 are fitted on the lower surface of a frame of the raw water supply and discharge unit 7 so that the unit 7 can easily taken out from the rack 1 lower section through the slope plates 6a, 6b to the exterior of the rack 1 and can readily be accommodated from the external in like manner to be installed within the rack 1 lower section.

Figure 12:
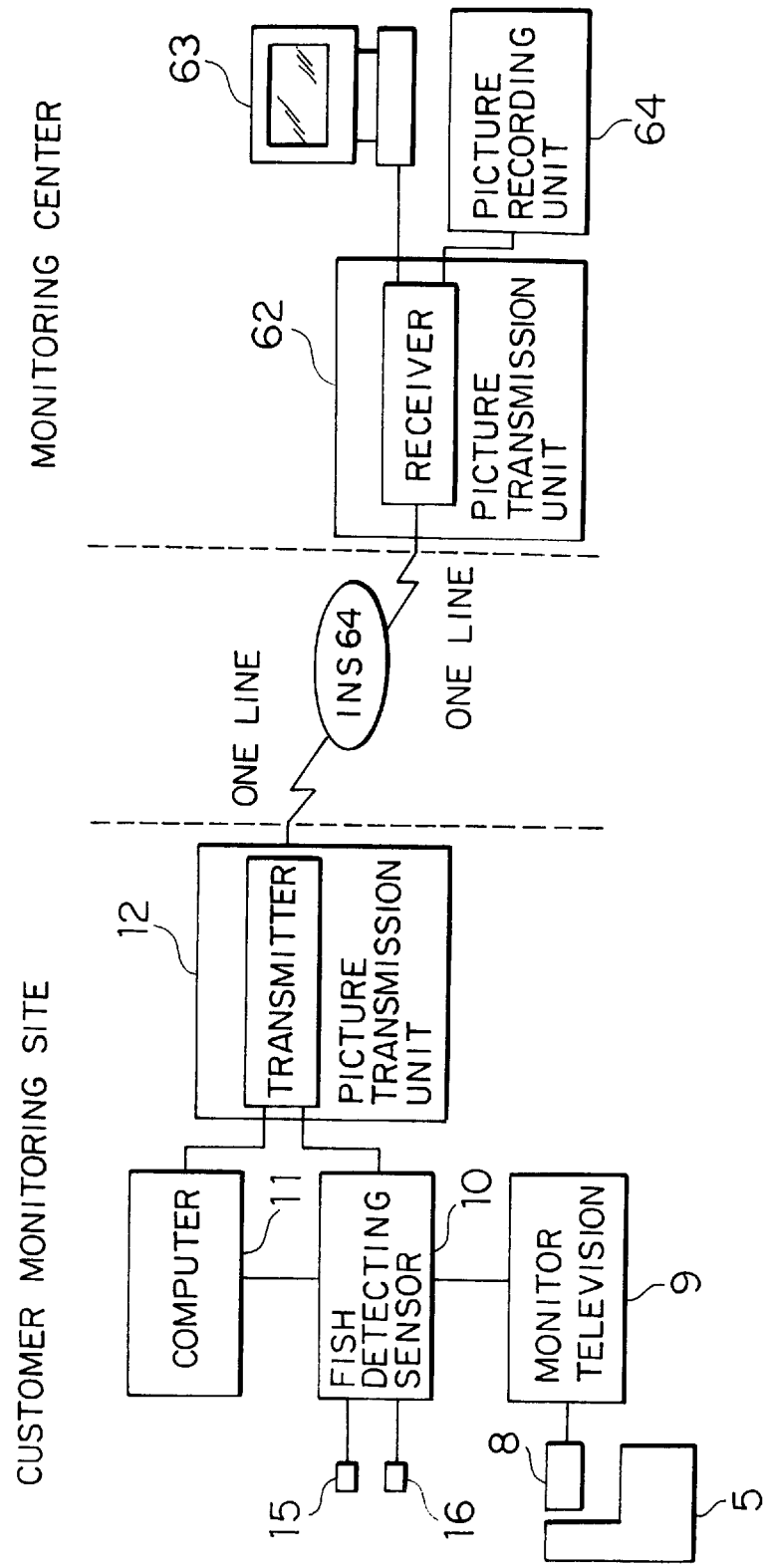
FIG. 12 is a block diagram useful for describing an image processing in the same water quality monitoring apparatus.

On the other hand, the image analysis section 3 being the upper section vertically accommodates a monitor television 9 for displaying a picture taken by the aforesaid video camera 8, a fish detecting sensor 10 for detecting the position of the fish on the basis of a picture signal from the camera 8 and for displaying this position as a sensor point on the monitor television 9, a computer 11 for analyzing the travelling locus, travelling speed and others of the fish on a signal from the sensor 10 to decide, on the basis of the actional pattern of the fish, whether the water quality abnormality occurs or not and for, when the water quality is abnormal, issuing an alarm signal to light an alarm lamp 15 and drive an alarm buzzer 16, and a picture transmission unit 12 for transmitting through a communication line (a public line or a private line), for example the INSnet 64, the image information of the monitor television 9 and the positional information from the computer 11 on the basis of the picture signal from the fish detecting sensor 10 (see the block diagram of FIG. 12). In this embodiment, the fish detecting sensor 10 and the computer 11 organize the image analysis means.

In this embodiment, as shown in FIG. 12, the picture transmission unit 12 is connected through a line of the INSnet 64 to a receiver 62 of a monitoring center and commonly transmits the image information including the positional information of the fish to the monitoring center at the occurrence of the alarm signal, while a monitor television 63 of a computer in the monitoring center displays the transmitted image so that the image and the fish actional pattern taken for when the water quality abnormality occurs can be watched in the monitoring center. In addition, when necessary, the monitoring center side can take in the picture information of the customer monitoring site through the aforesaid line to confirm the picture of the monitoring water tank in the customer monitoring side if necessary. If the picture transmission between the picture transmission unit 12 and the monitoring center is unnecessary, the arrangement for the transmission (picture transmission unit 12) is not always necessary.

In FIG. 1, numeral 13 designates an upper door for closing the aforesaid image analysis section 3 and numeral 14 depicts a lower door for closing the aforesaid fish monitoring section 2. The upper door 13 has a widow 13a made at the position corresponding to the screen of the monitor television 9 so that, even if the door 13 is in the closed condition, the screen of the monitor television 9 is watchable. Further, in the front surface side of the upper door 13, there are provided the aforesaid alarm lamp 15 which goes on in response to the alarm signal from the computer 11 and the aforesaid alarm buzzer 16 which raises an alarm sound in response to the same alarm signal. On the other hand, in the front surface side of the lower door 14, there is placed an alarm lamp 17 which lightens on the basis of the detection of the overflow (filled condition) or the abnormally decreased water level by floating switches 55, 59 which will be described later. In this embodiment, the alarm lamp 15 and the alarm buzzer 16 makes up the alarm means for giving notice of the water quality abnormality, while the alarm lamp 17 constitutes the alarm means for the notice of the water filled condition or the decreased water level.

Figure 2:
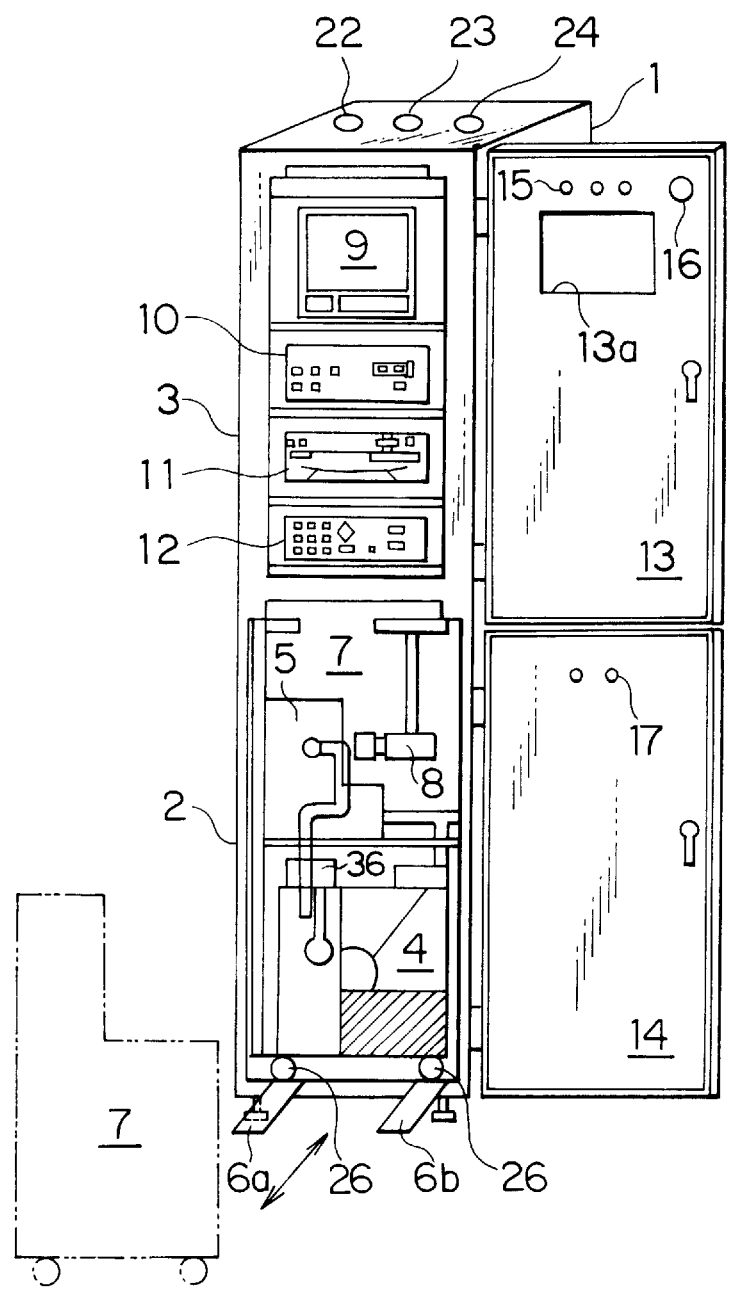
FIG. 2 is a perspective view showing a state where the same apparatus takes a door-open condition.
Figure 3:
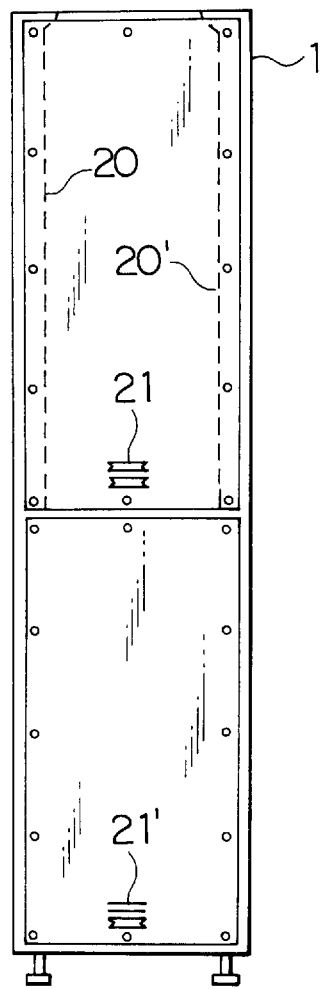
FIG. 3 is a rear elevational view showing the same apparatus.
Figure 6:
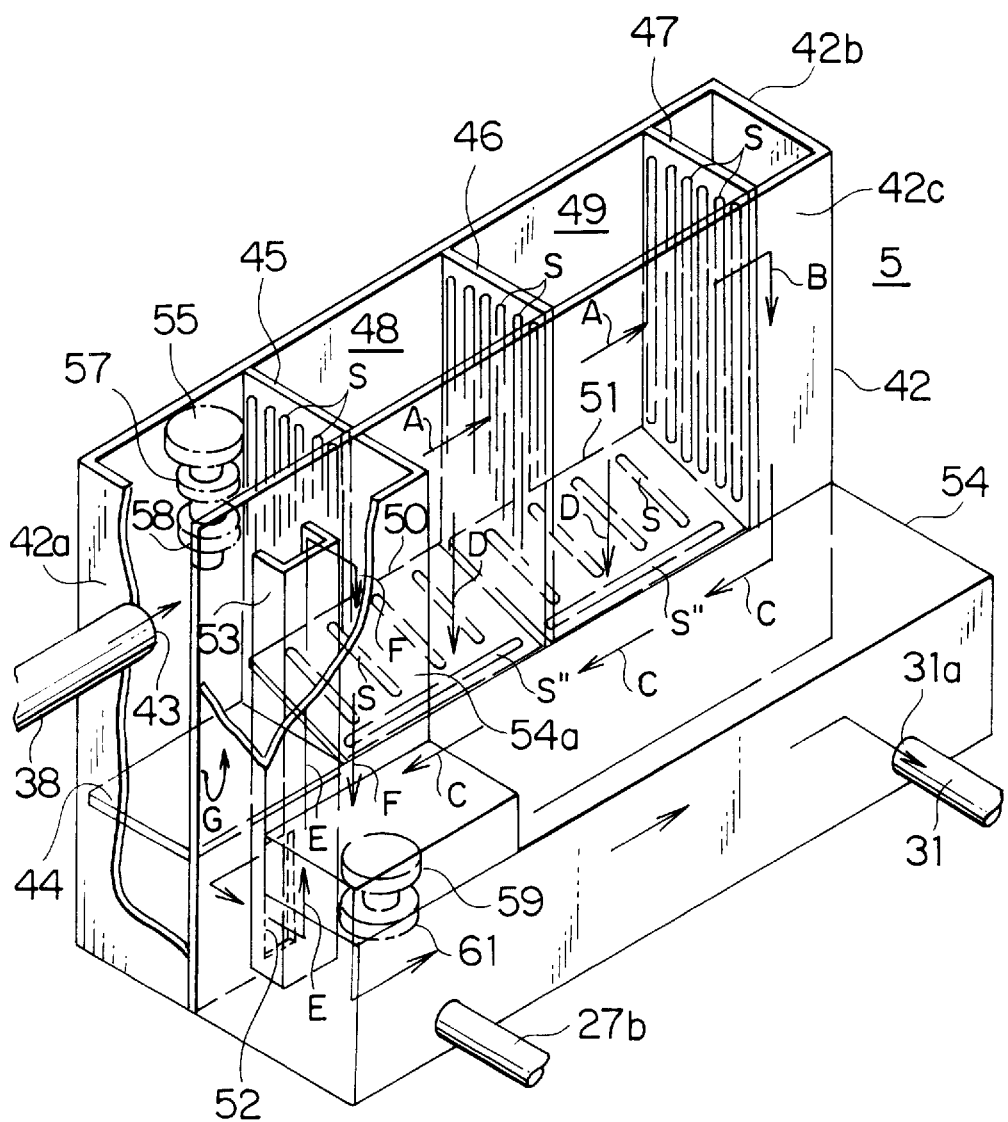
FIG. 6 is a partially broken and perspective view showing a monitoring water tank of the same apparatus.
Figure 7:
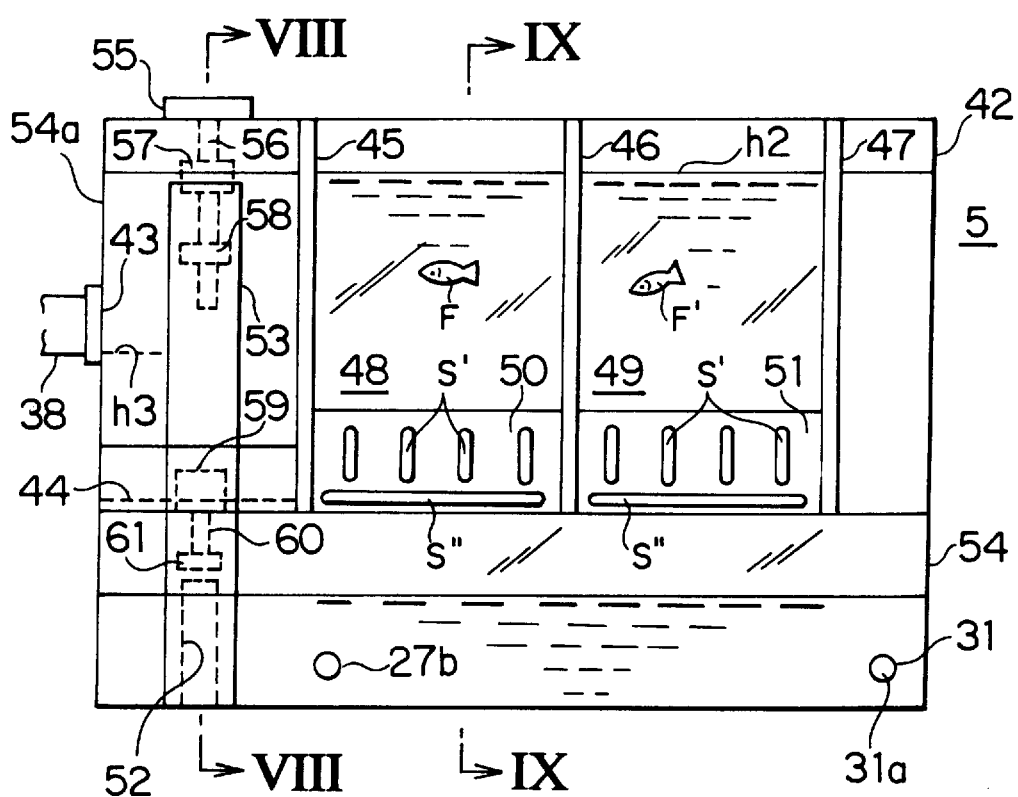
FIG. 7 is a front elevational view showing the same monitoring water tank.
Figure 8:
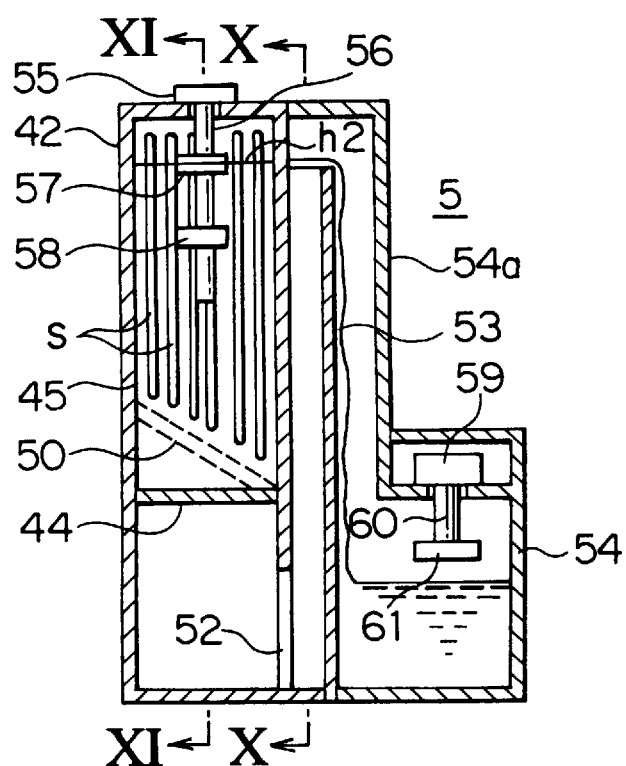
FIG. 8 is a cross-sectional view taken along a line X1–X1' of FIG. 7.
Figure 9:
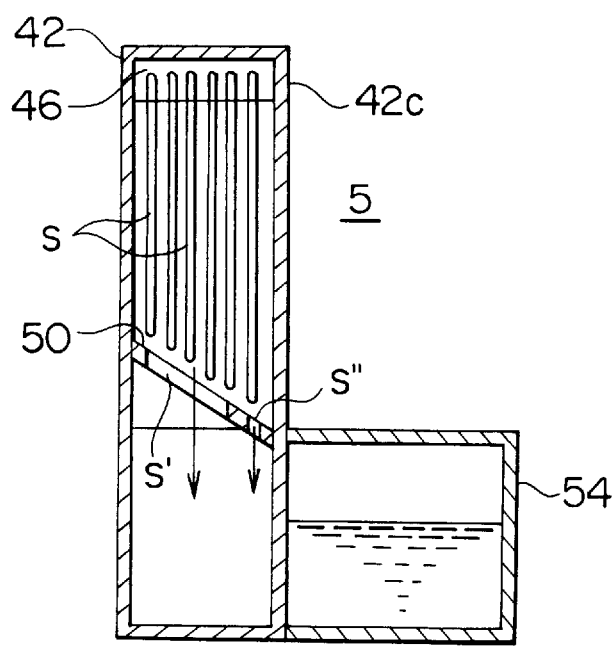
FIG. 9 is a cross-sectional view taken along a line X2–X2' of FIG. 7.
Figure 10:
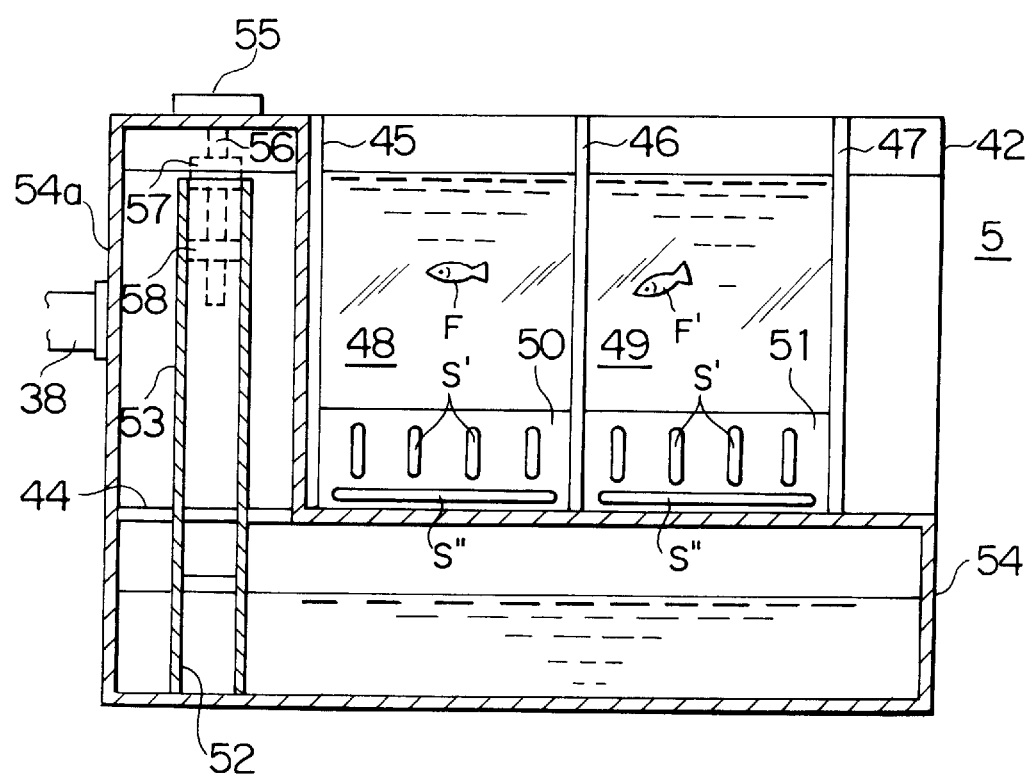
FIG. 10 is a cross-sectional view taken along a line Y1–Y1' of FIG. 8.
Figure 11:
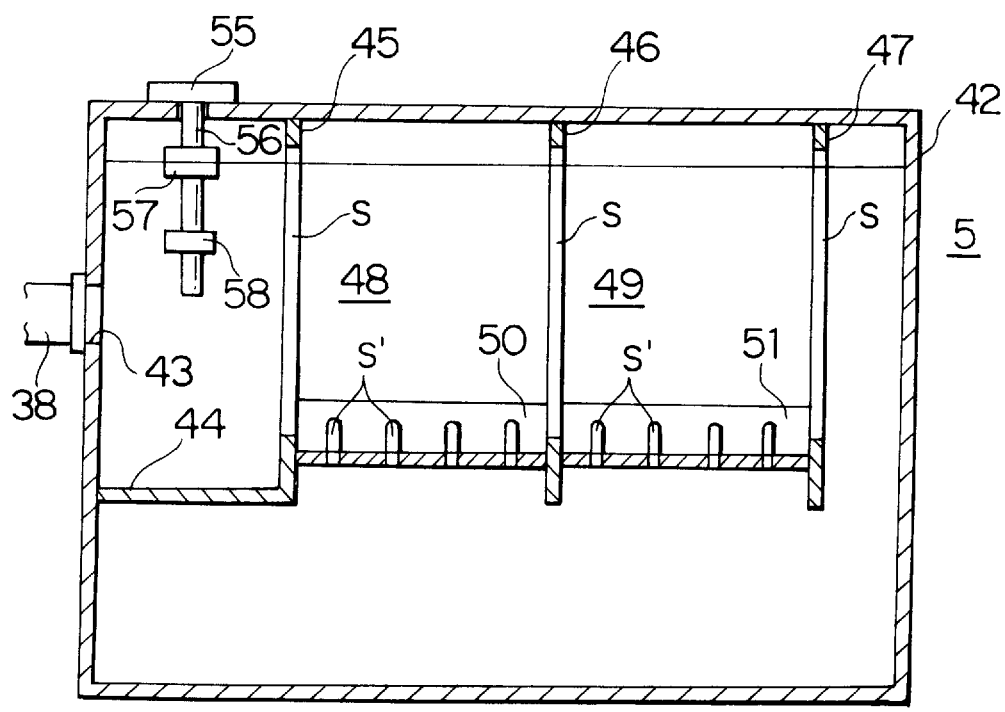
FIG. 11 is a cross-sectional view taken along a line Y2–Y2' of FIG. 8.

In FIGS. 1 to 3, numeral 18 represents a water supply opening made in a side surface of the rack 1 lower section, numeral 19 designates a water discharge opening made adjacent to the water supply opening 18, numerals 20, 20' depict ventilating ducts (see FIG. 3) installed on right-hand and left-hand wall surfaces of the internal rear surface of the rack 1 to vertically extend, numerals 21, 21' denote ventilating openings located o the rear surfaces of the upper and lower sections of the rack 1, and numerals 22 to 24 signify ventilating fans fitted on the top surface of the rack 1. These fans 22 to 24 suck the outside air through the ventilating openings 21, 21' and discharge it from the top surface thereof through the ventilating ducts 20, 20', which can prevent the cloudiness of a front surface plate 42c (see FIG. 6) of the monitoring water tank 5 and which can prevent the failure of the image equipment and the computer due to corrosion caused by the moisture, the water vapor or the like by means of the ventilation of the interior of the rack 1.

Figure 4:
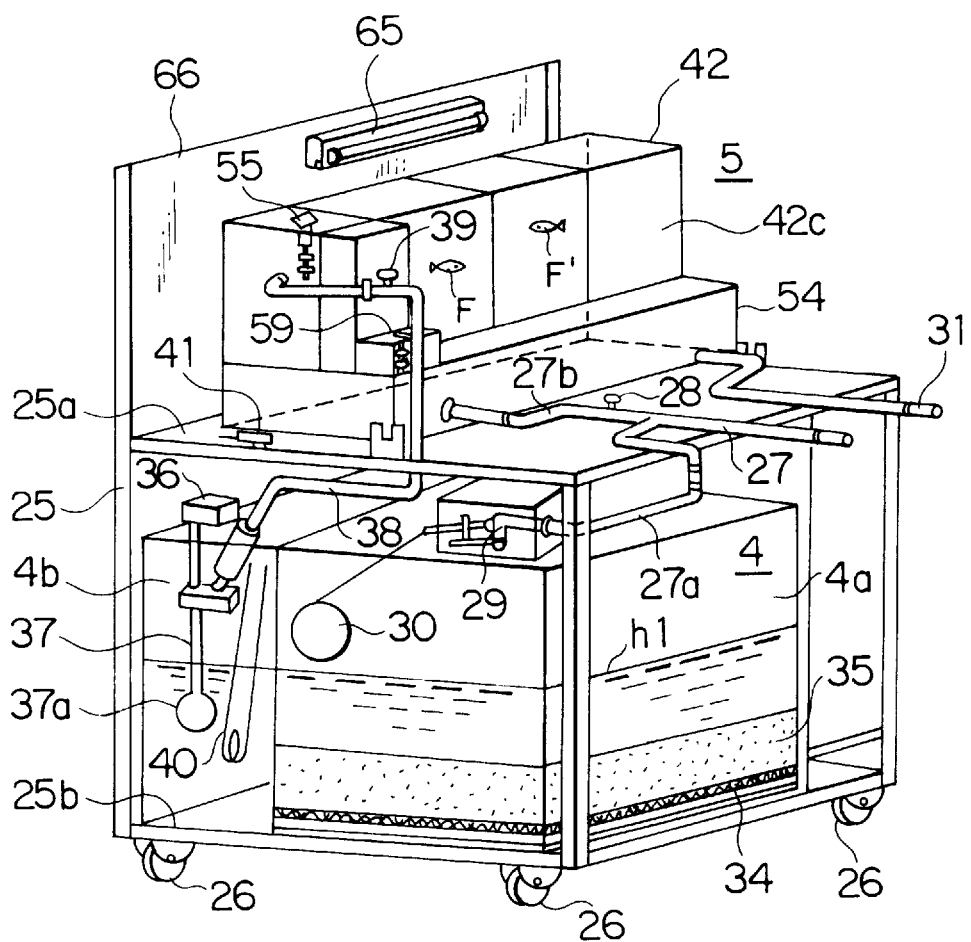
FIG. 4 is a perspective view showing a raw water supply and discharge unit of the same apparatus.

Referring to FIG. 4, a description will be taken hereinbelow of a structure of the aforesaid raw water supply and discharge unit 7. In this illustration, numeral 25 represents a frame vertically divided into two sections to comprise an upper section 25a and a lower section 25b which accommodate the monitoring water tank 5 and the filtering water receiving tank 4, respectively. The lower surface of the frame 25 is equipped with four casters (wheels) 26 so that the frame 25 is easily movable when being taken out from the rack 1 lower section. Further, numeral 27 signifies a water supply pipe coupled to the water supply opening 18 of the rack 1 to supply the raw water and is divided into a raw water supply pipe 27a for leading the supplied raw water to a filter tank 4a of the filtering water receiving tank 4 and a discharge pipe 27b for guiding the raw water through a sluice valve 28 to a discharge tank 54 which will be described later. The raw water supply pipe 27a has a water-amount adjusting valve 29 at its tip portion, which valve 29 is coupled to a ball tap 30 which floats on the water surface within the filtering tank 4a and moves up and down in accordance with the water level h1. Accordingly, the opening degree of the aforesaid valve 29 is controlled in accordance with the vertical position of the ball tap 30. The opening degree of the valve 29 is adjusted to always supply a constant amount of raw water (commonly, 2 to 3 liters per minute) to the filtering tank 4a when the water level assumes h1.

The aforesaid sluice valve 28 is for the purpose of adjusting the amount of the raw water flowing into the water supply pipe 27 and can increase and decrease the amount of the raw water to be fed into the water supply pipe 27 by its opening and closing operation. Thus, in cases where the water source is remote, the valve 28 is opened to a degree larger than usual to increase the raw water supply quantity, with the result that the time period taken from the drawing of the raw water from the water source to the introduction into this apparatus can be shortened to reduce the time lag from the drawing of the raw water to the detection. The raw water fed into the filtering water receiving tank 4 is kept to the aforesaid constant amount owing to the operation of the valve 29 irrespective of the water supply quantity depending on the valve 28, and hence the excessive raw water which does not come in the filtering water receiving tank 4 side is led through the aforesaid discharge pipe 27b into the discharge tank 54, which will be described later, and then discharged through a discharge opening 31a and a discharge pipe 31. In this embodiment, the water supply pipe 27, the raw water supply pipe 27a and the water amount adjusting valve 29 organize a raw water supply section.

Figure 5:
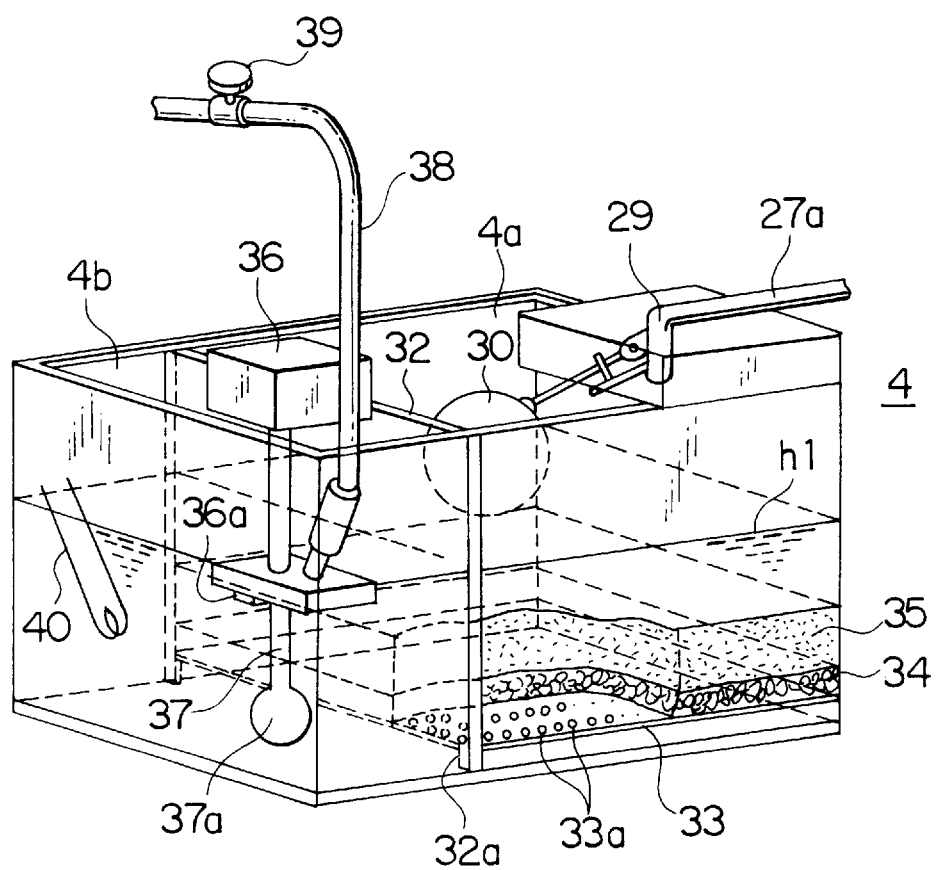
FIG. 5 is a partially broken and perspective view showing a filtering water receiving tank of the same apparatus.

As shown in FIG. 5, the filtering water receiving tank 4 supplies the raw water to the monitoring water tank 5 after removing dust and others contained therein. The filtering water receiving tank 4 is partitioned by a partition 32 into the filtering tank 4a and a water receiving tank 4b, and a gap 32a is defined in the lower end portion of the partition 32 to make communication between both the tanks 4a and 4b so that the raw water within the filtering tank 4a shifts through the gap 32a into the water receiving tank 4b. In the filtering tank 4a there are provided a bottom plate 33 placed right under the lower surface of the filtering tank 4a and having a plurality of water communicating holes 33a, a fiber-like filtering material (for example, cotton) 34 laid on the bottom plate 33, and river sand 35 laid on the fiber-like filtering martial 34. The raw water is filtered through these filtering devices and then introduced into the water receiving tank 4b.

Furthermore, numeral 36 denotes a water suction pump located an upper portion of the water receiving tank 4b and numeral 37 depicts a water suction pipe. The raw water within the water receiving tank 4b is sucked through a water suction opening 37a placed at a lower end portion of the water suction pipe 37 and is supplied through a connection pipe 38 into the monitoring water tank 5 positioned above it. A sluice valve 39 for the adjustment of the supplying water quantity is fitted in the middle of the connection pipe 38 so that the quantity of the water to be introduced into the monitoring water tank 5 is adjustable through the adjustment of the valve 39. The supplying water quantity to the monitoring water tank 5 is usually set to be equal to the supplying water amount (2 to 3 liters per minute) to the filtering water receiving tank 4. In the case that the water amount sucked by the water suction pump 36 is larger than the water amount to the monitoring water tank 5 introduced by the valve 39, the excessive raw water is discharged from a discharge opening 36a of the pump 36.

Still further, numeral 40 stands for a heater put in the water receiving tank 4b, with the temperature of the heater 40 being adjusted by a thermostat 41 on the basis of the water temperature detected by a water temperature sensor (not shown) positioned at an appropriate portion within the filtering water receiving tank 4 so that the temperature of the raw water is controlled to always become constant. In this embodiment, the water suction pump 36, the water suction pipe 37, the connection pipe 38 and others compose a raw water introduction section, whereas the discharge opening 31a (see FIG. 6) and the discharge pipe 31 makes up a raw water discharge section.

A structure of the monitoring water tank 5 will be described hereinbelow with reference to FIGS. 6 to 11. All the components of the monitoring water tank 5 are made with a transparent synthetic resin, and the monitoring water than 5 is composed of a rectangular parallelepiped like monitoring tank 42 for breeding fish F, F' under observation and a discharge tank 54 installed in the front surface side of the monitoring tank 42. In the monitoring tank 42, a inflow opening 43 coupled to the connection pipe 38 is located at a position slightly above a central portion of a left-hand side surface plate 42a of the tank 42. The aforesaid raw water flows through the inflow opening 43 into the monitoring tank 42 and establishes a first water flowing path from the left side to the right side (an arrow A direction) in a state that the water level is maintained to a given value h2 (see FIG. 7).

In the illustrations, numeral 44 signifies a water stream separating plate fixedly set at a position below a left-hand side surface plate 42a within the monitoring tank 42. after producing a water stream in the arrow A direction, the raw water creates a water stream advancing downwardly (an arrow B direction) in the vicinity of a right-hand side surface plate 42b and further produces a second water flowing path advancing from the right side to the left side in the opposite direction (an arrow C direction) below inclined plates 50, 51 which will be described later. Thus, the water flowing paths in the arrow A direction and in the arrow C direction are separated from each other and the raw water flow is straightened, besides the raw water introduced into the inflow opening 43 can be prevented from directly coming to the outflow opening 52 (see an arrow G).

Furthermore, numerals 45, 46 and 47 designate straightening plates successively and transversely fitted to be perpendicular to the first water flowing path of the monitoring tank 42 to divide the monitoring tank 42 into four sections, with the two sections existing at the central portion being used as monitoring sections 48, 49 for breeding the fish F, F' under observation. Each of the straightening plates 45, 46 and 47 has a plurality of elongated slits (water communicating holes) S extending in longitudinal directions and straighten the water stream in the arrow A direction in the monitoring sections 48, 49 so that poison or the like contained in the raw water evenly flows within the monitoring sections 48, 49. The width of each of the slits S is determined to inhibit that the fish F, F' under observation passes therethrough. Further, each of the monitoring sections 48, 49 are formed such that its width in the forward and backward directions becomes smaller than its width in the vertical and transverse directions so that within the monitoring sections 48, 49 the fish F, F' under observation can freely swim in the vertical ad transverse directions but can swim or make a U-turn somehow in the forward and backward directions. Accordingly, the degree of freedom of the movement in the vertical and transverse directions is made to be greater than the degree of freedom of the movement in the forward and backward directions (smaller width), with the result that the camera 8 can more clearly detect the movement of the fish F, F' under observation.

Still further, numerals 50, 51 denote inclined plates (perforated plates) for the removal of dust or the like which are fixedly fitted under between the straightening plates 45, 46 and under between the straightening plates 46, 47 to be inclined by a given angle in the forwarding direction and to be in parallel to the water stream made along the first water flowing path. Each of the inclined plates 50, 51 has a plurality of elongated longitudinal slits (water communicating holes) S' extending in the forward and backward directions and further has a transverse slit (water communicating hole) S" made at its front portion to extend in the transverse directions. Thus, the monitoring sections 48, 49 are formed in the spaces whose right and left sides and lower side are surrounded by the straightening plates 45 to 47 and the inclined plates 50, 51. The water stream in the arrow A direction and a downward water stream D occur within the monitoring sections 48, 49, and the inclined plates 50, 51 cause the dust, duckweed and others coming down due to the downward water flow within the monitoring sections 48, 49 or their dead weights to fall downwardly through the slits S' thereof or to slip downwardly along their inclined surfaces to drop downwardly through the slits S" (see arrows in FIG. 9). In addition, they prevent the dust, duckweed and others once coming down to below the inclined plates 50, 51 from flowing in the opposite direction, with the result that the stay and accumulation of the dust and duckweed in the interiors of the monitoring sections 48, 49 are avoidable to keep the interiors of the monitoring sections 48, 49 in a clean condition.

Moreover, numeral 52 depicts an outflow opening singly made in a left and lower side of a front surface plate 42c of the monitoring water tank 42 and in the downstream side of the second water flowing path, numeral 53 denotes an overflow cylinder communicated at its lower end portion with the outflow opening 52 and provided in the external front surface side of the front surface plate 42c, and numeral 54 stands for a discharge tank placed in the front surface side lower portion of the monitoring tank 42 in a state that the front surface plate 42c is interposed therebetween. In the upper surface left side of the tank 54 there is installed a discharge cylinder 54a which surrounds the overflow cylinder 53. The lower end portion of the overflow cylinder 53 is, as mentioned before, communicated with the outflow opening 52 and the top surface thereof is in an open state, and the upper end portion thereof is made to be slightly lower in position than the upper end portion of the monitoring tank 42. Therefore, the raw water from the arrow C direction in the second water flowing path within the monitoring tank 42 comes out through the outflow opening 52 to enter the overflow cylinder 53 and then goes upwardly (see an arrow E) within the overflow cylinder 53 to come down within the discharge cylinder 54a (see an arrow F) after overflowing from its top surface opening to flow into the discharge tank 54. The raw water entering the discharge tank 54 is discharged through the discharge opening 31a and the discharge pipe 31 to the external and afterwards reaches a processing tank (not shown) or the like. Accordingly, in the water flowing path from the aforesaid filtering tank 4a to the discharge pipe 31, the water whose amount is equal to the constant water amount supplied to the filtering tank 4a is fed to the monitoring water tank 5 and the water equal in quantity to the supplied water is discharged from the discharge pipe 31. When the sluice valve 28 is opened, the excessive raw water flowing from the discharge pipe 2b into the discharge tank 54 is also discharge through the interior of the discharge tank toward the discharge pipe 31.

Still further, numeral 55 signifies a float switch (detection means) provided above the inflow opening 43 of the monitoring tank 42 (see FIGS. 7 to 11). An overflow detection float 57 and a water decrease detection float 58 are fitted over a shaft 56, and the water decrease detection float 58 ordinarily floats at a given position in the water while the overflow detection float 57 floats at a given position on the water surface. In case that the water decrease detection float 58 is exposed to the water surface and goes down along the shaft 56 to a given position because the water level falls due to the failure or the like of the pump, or in case that the water level rises so that the overflow detection float 57 is submerged and goes up along the shaft 56 to a given position, the float switch 55 detects the fall of the water level or the overflow to issue the alarm signal, and the alarm pump 17 on the lower door of the rack 1 goes on in response to the alarm signal.

Moreover, numeral 59 represents a float switch (detection means) located above the discharge tank 54, which is constructed such that an overflow detection float 61 is fitted over a shaft 60. Usually, the float 61 stays at the lowermost position of the shaft 60. If the water level within the discharge tank 54 rises so that the float 61 is submerged and goes up to the water surface along the shaft 60, the float switch 59 detects this state to produce a signal so that the alarm lamp 17 on the lower door of the rack 1 lights in response to the same signal to give notice of the abnormal rise of the water level within the discharge tank 54. In the illustrations, numeral 65 represents a fluorescent lamp for illuminating the monitoring water tank 5 from the back side and numeral 66 denotes a backing plate for the frame 25.

Secondly, a description will be taken hereinbelow of an operation of the apparatus thus constructed according to this invention. The raw water drawn from a water source such as a pond and a river through a water intake pipe (not shown) or the like is introduced through the water supply opening 18 of the rack 1 into the water supply pipe 27 and further comes through the raw water supply pipe 27a and the water amount adjusting valve 29 into the filtering tank 4a of the filtering water receiving tank 4. Further, when the water level within the filtering tank 4a reaches the given value h1, depending upon the opening degree of the water amount adjusting valve 29 based on the position of the ball tap 30, the incoming water amount is limited to a constant quantity of 2 to 3 liters per minute. The raw water entering the filtering tank 4a is filtered through the river sand 35 and the fiber-like filtering material 34 and then introduced through the gap 32a into the water receiving tank 4b. The raw water reaches a given level within the water receiving tank 4b and is sucked by the water suction pump 36 through the water suction opening 39 to flow through the water suction pipe 37, the connection pipe 38 and the sluice valve 39 and further through the inflow opening 43 into the monitoring tank 42 of the monitoring water tank 5 installed in the aforesaid upper section. At this time, since the amount of the water flowing into the monitoring tank 42 through the sluice valve 39 is set to be equal to the quantity of the water introduced into the filtering tank 4a, the amount of the water coming into the monitoring tank 42 coincides with the quantity of the water entering the filtering tank 4a.

The raw water flowing into the monitoring tank 42 causes the water level within the monitoring tank 42 to gradually rise, and it flows through the outflow opening 52 of the front surface plate 42c into the overflow cylinder 53 (see the arrows C and E) to raise the water level within the overflow cylinder 53. When reaching the water level h2 substantially equal to the upper end portion of the overflow cylinder 53, the raw water overflows from the cylinder 53 to enter the discharge tank 54 (see the arrow F). Accordingly, the water level within the monitoring tank 42 is maintained to the level h2 substantially equal to the upper end portion of the overflow cylinder 53. The raw water introduced into the discharge tank 54 is discharged from the discharge pipe 31 in a state with keeping a given water level. Thus, with the water level within the monitoring tank 42 being maintained to h2, the raw water produces a series of water flowing path of its flowing through the path made up of the filtering tank 4a, the water receiving tank 4b, the monitoring tank 42 and the discharge tank 54 by turns and then discharged from the discharge pipe 31 of the discharge tank 54. Further, in the state of the formation of this water flowing path, the water streams from the inflow opening 43 to the outflow opening 52 in the arrow A, B and C directions take place within the monitoring tank 42, besides the downward water stream in the arrow D direction occurs within the respective monitoring sections 48, 49.

If the water source is remote, the sluice valve 28 is more opened than usual so that the quantity of the water introduced into the water supply pipe 27 increases. Thus, the amount of the raw water supplied to the water supply pipe 27 can increase and the time period taken until the raw water drawn from the water source is introduced into this apparatus can be shortened to decrease the time lag from the drawing to the monitor in this apparatus. In a state where the above-mentioned supply and discharge of the raw water are continuously made, the fish F, F' to be bred such as killifishes are put in the monitoring sections 48, 49 of the monitoring tank 42 and the actions of the fish F, F' under observation are photographed through the video camera 8 installed at the position opposed to the front surface plate 42c of the monitoring tank 42. At this time, since the water flows along the first water flowing path in the arrow A direction within the monitoring sections 48, 49, the environment close to the natural river or the like is attainable, with the result that it is possible to breed the fish F, F' in a good condition for a long time without applying stress to the fish F, F'.

The dust and grown duckweed within the monitoring tank 42 and the dust or the like removed from the inner surfaces of the monitoring sections 48, 49 by the water stream in the arrow A or D direction shift downwardly therein by means of the water stream in the arrow D direction or their dead weight and further drop downwardly through the longitudinal slits S' of the inclined plates 50, 51 to below the inclined plates 50, 51. In addition, the dust or the like dropping onto the inclined surfaces of the inclined plates 50, 51 roll forwardly along the inclined surface thereof to fall through the transverse slits S" to below the inclined plates 50, 51. Further, the dust once dropping to below the inclined plates 50, 51 is shifted in the left-hand direction by the water stream C and is prevented by the blocking effects of the inclined plates 50, 51 from flowing in the opposite direction. Still further, since the water stream always occurs in the inner surface side of the front surface plate 42c of the monitoring sections 48, 49, it is possible to prevent the dust or the like from adhering to the inner surface including the monitoring section front surfaces and to always keep the interiors of the monitoring sections 48, 49 in a cleaned condition so that the growth of duckweed or the like is suppressible therein.

Furthermore, the dust, duckweed or the like dropping to below the inclined plates 50, 51 and coming to below the inclined plates 50, 51 along the water stream in the arrow A, B and C directions comes out through the outflow opening 52 by the water stream in the arrow C direction and then rises within the overflow cylinder 53 along the water streams in the arrow E and F directions and subsequently drops from the top surface of the cylinder 53 to enter the discharge tank 54, with it being discharged through the discharge pipe 31. Thus, the monitoring tank 42 and the discharge tank 54 communicate with each other through only the overflow cylinder 53, and hence the dust, duckweed or the like once introduced into the discharge tank 54 does not go toward the monitoring tank 42, with the result that it is possible to prevent the dust, duckweed or the like from staying and being accumulated within the monitoring tank 42.

On the other hand, in case that the supply of the raw water into the monitoring water tank 5 stops due to the failure or the like of the water suction pump 36, the water level gets to fall to become lower than the upper end portion of the overflow cylinder 53 and then reaches the lower limit position h3 (see FIG. 7) of the inflow opening 43 because of the back flow in the connection pipe 38 or the like. However, the water level is maintained at this position after that. Accordingly, even if the water supply into the monitoring tank 42 stops due to the failure of the pump or the like, the water level within the monitoring tank 42 can be kept at the position h3 to protect the fish F, F' under observation. Further, when the water level goes down, the float switch 55 detects the water level falling state by its water decrease detection float 58 so that the alarm lamp 17 on the lower door of the rack 1. For these reasons, the apparatus operator and other persons can easily know the fact that the water level within the monitoring tank 42 abnormally falls. On the other hand, if the water level within the monitoring tank 42 rises due to the adjustment failure of the sluice valve 39 or the like, the overflow detection float 57 of the float switch 55 is raised to detect the occurrence of the overflow, so that the alarm lamp 17 on the lower section of the rack 1 goes on. Thus, the operator and others can easily know the fact that the overflow from the monitoring tank 42 occurs.

Although as described above the monitoring water tank 5 has a structure to prevent the attachment of the duckweed or the like to the utmost, since the use for a long time allows the attachment of the dust or duckweed thereto, the periodic cleaning (for example, once for 2 to 3 months) of the monitoring water tank 5 and the filtering water receiving tank 4 or the replacement of the filtering material becomes necessary. In such a case, the lower door 14 of the rack 1 is opened and the slope plates 6a, 6b are set so that the raw water supply and discharge unit 7 is taken out from the lower section 2 thereof using the slope plates 6a, 6b (see FIG. 2) and shifted to a different place to undergo the cleaning. Further, during this cleaning a different raw water supply and discharge unit 7 is placed in the lower section 2 of the rack 1 so that the water quality monitoring operation can continuously be done.

The picture signal from the video camera 8 is inputted into the fish detecting sensor 10 where the picture signal is processed to continuously detect the position or the like of the fish F, F' under observation and a position signal corresponding to that position is fed to the computer 11 which in turn, recognizes the actional pattern of the fish on the basis of the position signal. Thereafter, the actional pattern recognized is compared with a fish abnormal actional pattern stored in advance to check whether the actional pattern is abnormal or not. If the decision is made to the abnormality of the fish actional pattern, the computer 11 issues the alarm signal indicative of the abnormality of the water quality so that the alarm buzzer 16 and the alarm lamp 15 are driven in accordance with the alarm signal to give notice of the abnormality of the water quality.

When transmitting the picture information, on the basis of the generation of the alarm signal from the computer 11, the picture information from the fish detecting sensor 10 and the position signal (a signal representative of the position of the fish under observation) from the computer 11 are given to the picture transmission unit 12 where its transmitter transmits them through one line of the INSnet 64 to the monitoring center. In the monitoring center, the receiver 62 receives the picture information transmitted and then the monitor television 63 reproduces it. Accordingly, in the monitoring center, the picture taken at the occurrence of the alarm can be watched through the monitor television 63, and the picture information can be recorded in a picture recording unit 64. Further, in the monitoring center, it is possible to inform the customer monitoring site having the water quality monitoring apparatus of the situation of the water quality contamination in accordance with the picture on the monitor television 63 and further to provide long-term data or the like to the customers on the basis of the recorded picture information. If required, the information center side can derive the picture information from the customer monitoring site irrespective of the issue of the aforesaid alarm signal to check the picture of the customer's monitoring water tank when necessary.

In this embodiment, the two monitoring sections (48, 49) are provided in the monitoring tank 42 and the two fish are put therein, respectively. This is for more surely conducting the monitoring operation in such a manner that the decision to the abnormality of the water quality is not made until the two fish respectively show the actional pattern taken at the occurrence of the water quality abnormality as a result of the simultaneous analysis of the action of the fish in the two places. If such an operation is unnecessary, it is possible that one monitoring section is made in the monitoring tank 42 and one fish is put therein.

As described above, the water quality monitoring apparatus according to the present invention can create water streams straightened within the monitoring sections 48, 49 to produce an environment close to the natural rivers or the like and hence can breed fish F, F' in a good condition without applying stress to the fish F, F'. Thus, the sensitive response of the fish in the raw water is maintainable and the more certain water quality monitoring is possible. In addition, the dust, duckweed or the like produced within the monitoring sections 48, 49 or removed from their front surfaces by means of the water streams within the monitoring sections 48, 49 drops by the downward water streams within the monitoring sections 48, 49 or by its dead weight to go down through the slits S' and S" of the inclined plates 50, 51 to below the inclined plates 50, 51. Further, since the dust or the like dropping to below the inclined plates 50, 51 does not go in the opposite direction, the dust or the like within the monitoring sections 48, 49 is removable to suppress the growth of duckweed or the like.

Furthermore, since the raw water supply and discharge unit 7 is grouped and placed within the single frame 25, the size of the whole apparatus is reducible, and since the casters 26 are fitted on the lower portion of the frame 25, the apparatus itself is easily movable, which is extremely convenient in changing the location and in cleaning the water tanks. In addition, when the raw water is drawn from a remote water source, the sluice valve 28 is more opened than usual to increase the water supply quantity to the water supply 27. Thus, even if the water source is remote, the time lag from the drawing to the monitoring in this apparatus is reducible. Further, since the water receiving tank 4b which is equipped with the water suction pump 36, the heater 40 and others is installed integrally with the filtering tank 4a and the raw water is supplied through the gap 32a of the partition 32 to the water receiving tank 4b, the communication pipes or the like become unnecessary between both the tanks, with the result that the size reduction of the raw water supply and discharge unit 7 is possible.

Still further, since the image equipment and the electronic equipment are accommodated in the upper section of the rack 1 while the raw water supply and discharge unit 7 is encased in the lower section thereof and the whole water quality detecting apparatus is housed in the single rack, the entire apparatus is reducible in size and an excessive location space is unnecessary. In addition, since the raw water supply and discharge unit 7 is detachable from the lower section 2 of the rack 1, at the cleaning of the tanks the supply and discharge unit 7 can readily be taken out from the rack lower section 2 and movable therefrom, and the water quality monitoring apparatus extremely excellent in maintenance is realizable. Further, while the raw water supply and discharge unit 7 is out, a different raw water supply and discharge unit can be put in the same rack lower section to continue the water quality monitoring operation without interrupting the water quality monitoring operation whenever, for example, cleaned. Still further, because the upper door 13 of the rack 1 has the window 13a corresponding in position to the internal monitor television 9, even if the door 13 is in the closed state, it is possible to check the state of the fish under observation from the external. Moreover, when the abnormality of the water quality is detected, the notice of the water quality abnormality can easily be given through the alarm lamp 15 and the alarm buzzer 16.

Even if water vapor is produced within the rack 1 due to the heater 40 in the water receiving tank 4b or the like, the ventilating fans 22 to 24 can ventilate the interior of the rack 1, thereby preventing the failure of the image equipment and the electronic equipment due to corrosion or the like and preventing the cloudiness on the front surface plate 42c of the monitoring tank 42. Further, the water level h2 within the monitoring tank 42 is maintainable to a constant level substantially equal to the position of the upper end portion of the overflow cylinder 53. Still further, in case that the introduction of the raw water from the inflow opening 43 stops for some reason, the water level within the monitoring tank 42 lowers to be lower than the upper end portion position of the overflow cylinder 53 and further becomes slightly lower due to the back flow in the inflow opening 43 or other causes. However, the water level does not fall to below the inflow opening 43. For this reason, the fish under observation does not die even if an unpredictable situation such as the fall of the water level occurs. Thus, it is possible to repair the breakdown portions afterwards and possible to quickly continue the monitoring operation after the water level is restored. In addition, since the dust or the like flowing from the outflow opening 52 into the overflow cylinder 53 reaches the discharge tank 54 and does not return to the monitoring tank 42, with the result that the dust or the like is not accumulated within the monitoring tank 42 and the interior of the monitoring tank 42 can always be maintained in a clean state.

Since in the monitoring water tank 5 there is provided the float switches 55, 59 for detecting the filled and decreased conditions of the raw water, in case that, for example, the raw water comes into the filled condition or an abnormally decreased condition due to the failure of the pump 36 or the like, the notice on the filled condition or the decreased condition can be given by raising an alarm on the basis of the detection.

Furthermore, when the computer 11 detects the abnormality of the water quality, the picture information is sent to the picture transmission unit to be transmit through the communication line (a public line or a private line) to a monitoring center standing at a different place, so that the center can analyze the action of the fish under observation at the occurrence of the abnormality through a monitor television 63. Further, the monitoring center can give various kinds of information and instructions to the customer monitoring side on the basis of the analysis result.

As described above, the water quality monitoring apparatus according to the present invention can create water streams straightened within the monitoring sections, produce an environment close to the water streams of the natural rivers or the like and can breed fish in a good condition without applying stress to the fish, thus surely carrying out the water quality monitoring operation. In addition, the dust, duckweed or the like produced within the monitoring sections is removable through the war communicating holes of the perforated plates toward below the perforated plates, and the perforated plates can prevent the back flow of the dust or the like to the monitoring sections so that the generation of dust, the growth of duckweed or the like are suppressible.

Furthermore, since the raw water supply and discharge unit 7 is grouped and placed within the single frame, the size of the whole apparatus is reducible, and since the wheels are fitted on the lower portion of the frame, the apparatus itself is easily movable, which is extremely convenient in changing the location and in cleaning the water tanks. In addition, since the water receiving tank for receiving the raw water filtered is installed integrally with the filtering tank, the connection pipe or the like between both the tanks becomes unnecessary, with the result that the raw water supply and discharge unit is reducible in size.

Still further, since the image equipment and the electronic equipment are accommodated in the upper section of the housing while the frame is formed in the lower section and the raw water supply and discharge unit 7 is wholly encased in the single, the entire apparatus is reducible in size and an excessive location space is unnecessary. In addition, since the frame is detachable from the lower section of the housing, at the cleaning of the tanks or the like the frame can readily be taken out from the housing lower section and movable therefrom, and the water quality monitoring apparatus extremely excellent in maintenance is realizable. Further, while the frame is out, a frame with a different raw water supply and discharge means can be put in the housing lower section to continue the water quality monitoring operation without interrupting the water quality monitoring operation whenever, for example, cleaned. Still further, because the housing upper section has the window corresponding in position to the internal monitor television, it is possible to check the state of the monitoring water tank from outside the housing. Moreover, when the abnormality of the water quality is detected, the operator can easily know the water quality abnormality by means of the alarm from the alarm means.

Even if water vapor is produced within the housing due to the heater in the water tank or the like, the ventilating equipment can ventilate the interior of the housing, thereby preventing the failure of the image equipment and the electronic equipment due to corrosion or the like. Further, the water level within the monitoring water tank is maintainable to a constant level substantially equal to the position of the upper end portion of the overflow cylinder. Still further, in case that the introduction of the raw water from the inflow portion stops for some reason, the water level does not fall to below the inflow section. For this reason, the fish under observation does not die even if an unpredictable situation such as the fall of the water level occurs. Thus, it is possible to repair the breakdown portions afterwards. In addition, since the dust or the like flowing through the overflow cylinder into the discharge tank does not return to the monitoring water tank, it is possible to prevent the dust or the like from being accumulated within the monitoring water tank.

Since in the monitoring water tank there is provided the detection means for detecting the filled and decreased conditions of the raw water, in case that, for example, the raw water comes into the filled condition or a decreased condition due to the failure of the pump or the like, the notice of the filled condition or the decreased condition can be given by raising an alarm or the like on the basis of the detection by the detection means.

Furthermore, when the image analysis means detects the abnormality of the water quality, the picture signal is sent to the picture transmission means to be transmit through the communication line to a monitoring center standing at a different place, so that the center can analyze the action of the fish under observation at the occurrence of the abnormality through a monitor television. Further, the monitoring center can give various kinds of instructions to the operator or others existing in the location of the water quality monitoring apparatus on the basis of the analysis result.

It should be understood that the foregoing relates to only a preferred embodiment of the present invention, and that it is intended to cover all changes and modifications of the embodiment of the invention herein used for the purpose of the disclosure, which do not constitute departures from the spirit and scope of the invention.

What is claimed is:

1. A water quality monitoring apparatus comprising:
    a monitoring water tank for accommodating raw water to breed fish under observation said raw water;
    a video camera for photographing said fish from a front surface side of said monitoring water tank; and
    image analysis means for analyzing a picture taken by said video camera to monitor a quality of said raw water within said monitoring water tank,
    wherein said monitoring water tank includes:
        an inflow opening made in one side surface of said monitoring water tank to form a first water flowing path running from said one side surface toward the other side surface thereof which is in opposed relation to said one side surface;
        a plurality of straightening plates each having a plurality of water communicating holes and provided in said first water flowing path to be perpendicular thereto and to be separated from each other to define a monitoring section for breeding said fish therebetween;
        a perforated plate having a plurality of water communicating holes and placed below and in parallel to said first water flowing path to establish a second water flowing path coupled to said first water flowing path under said plurality of straightening plates; and
        an outflow opening made in said second water flowing path.

2. An apparatus as defined in claim 1, further comprising:
    an overflow cylinder located outside said monitoring water tank and having an opening at its upper portion; and
    a discharge tank situated outside said overflow cylinder,
    wherein an upper end portion of said overflow cylinder is made to be slightly lower in position than an upper end portion of said monitoring water tank, and the interior of said overflow cylinder is communicated through said outflow opening with said monitoring water tank, and said raw water overflown from said upper portion opening of said overflow cylinder is discharged through said discharge tank.

3. An apparatus as defined in claim 1, further comprising:
    detection means for detecting a filled condition and decreased condition of said raw water within said monitoring water tank; and
    alarm means for raising an alarm on the basis of the detection of one of the filled condition and the decreased condition by said detection means.

4. An apparatus as defined in claim 1, wherein said image analysis means includes picture transmission means for transmitting to a communication line a picture signal produced when detecting an abnormality of the water quality.

5. A water quality monitoring apparatus comprising:

a filtering tank for filtering raw water;

a monitoring water tank for accommodating said raw water filtered through said filtering tank to breed fish under observation in said raw water;

a frame for supporting said filtering tank and said monitoring water tank;

a plurality of wheels fitted on a lower portion of said frame;

a raw water supply section for supplying said raw water to said filtering tank;

a raw water introduction section for introducing said raw water filtered through said filtering tank into said monitoring water tank;

a raw water discharge section for discharging said raw water from said monitoring water tank;

a video camera for photographing said fish within said monitoring water tank; and image analysis means for analyzing a picture taken by said video camera to monitor a quality of said raw water within said monitoring water tank.

6. An apparatus as defined in claim 5, further comprising a water receiving tank placed on said frame for accepting said raw water filtered through said filtering tank, said raw water introduction section introducing said raw water within said water receiving tank into said monitoring water tank, and said water receiving tank and said filtering tank being constructed integrally with each other in a state that a partition is interposed therebetween.

7. An apparatus as defined in claim 5, further comprising:

a housing divided into upper and lower sections; and a monitor television housed within said upper section of said housing for displaying a picture taken by said video camera, wherein said frame, together with said filtering tank and said monitoring water tank, is detachably housed within said lower section of said housing, and said video camera is disposed within said lower section of said housing to be in opposed relation to said monitoring water tank, and a side surface of said lower section of said housing has a water supply opening and a water discharge opening coupled to said raw water supply section and said raw water discharge section, respectively, and said image analysis means is housed within said upper section of said housing.

8. An apparatus as defined in claim 7, further comprising alarm means for raising an alarm when said image analysis means detects an abnormality of the water quality, said upper section of said housing having a window in its front surface so that a screen of said monitor television is seen through said window from the external.

9. An apparatus as defined in claim 7, further comprising a ventilating opening made in said housing and a ventilating device coupled to said ventilating opening for ventilating the interior of said housing.

10. An apparatus as defined in claim 5, wherein said monitoring water tank includes:

an inflow opening made in one side surface of said monitoring water tank to form a first water flowing path running from said one side surface toward the other side surface thereof which is in opposed relation to said one side surface, and communicated with said raw water introduction section;

a plurality of straightening plates each having a plurality of water communicating holes and provided in said first water flowing path to be perpendicular thereto and to be separated from each other to define a monitoring section for breeding said fish therebetween;

a perforated plate having a plurality of water communicating holes and placed below and in parallel to said first water flowing path to establish a second water flowing path coupled to said first water flowing path under said plurality of straightening plates; and an outflow opening made in said second water flowing path and coupled to said raw water discharge section.

11. An apparatus as defined in claim 5, further comprising:

an overflow cylinder located outside said monitoring water tank and having an opening at its upper portion; and a discharge tank situated outside said overflow cylinder, wherein an upper end portion of said overflow cylinder is made to be slightly lower in position than an upper end portion of said monitoring water tank, and the interior of said overflow cylinder is communicated through said outflow opening with said monitoring water tank, and said raw water overflown from said upper portion opening of said overflow cylinder is discharged through said discharge tank.

12. An apparatus as defined in claim 5, further comprising:

detection means for detecting a filled condition and decreased condition of said raw water within said monitoring water tank; and alarm means for raising an alarm on the basis of the detection of one of the filled condition and the decreased condition by said detection means.

13. An apparatus as defined in claim 5, wherein said image analysis means includes picture transmission means for transmitting to a communication line a picture signal produced when detecting an abnormality of the water quality.

* * * * *